US008653318B2

(12) United States Patent
Liu et al.

(10) Patent No.: US 8,653,318 B2
(45) **Date of Patent: *Feb. 18, 2014**

(54) PROCESS FOR PREPARING AN ALKYLATE

(75) Inventors: Zhichang Liu, Changping Beijing (CN); Chunming Xu, Changping Beijing (CN); Rui Zhang, Changping Beijing (CN); Xianghai Meng, Changping Beijing (CN); Ana Cecilia Patroni, Amsterdam (NL); Peter Anton August Klusener, Amsterdam (NL); Albertus Vincentius Petrus Van Den Bosch, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/388,470

(22) PCT Filed: Aug. 6, 2010

(86) PCT No.: PCT/EP2010/061488

§ 371 (c)(1), (2), (4) Date: Mar. 23, 2012

(87) PCT Pub. No.: WO2011/015654

PCT Pub. Date: Feb. 10, 2011

(65) Prior Publication Data

US 2012/0172647 A1 Jul. 5, 2012

(30) Foreign Application Priority Data

Aug. 6, 2009 (WO) ................ PCT/CN2009/000887

(51) Int. Cl.
*C07C 2/54* (2006.01)

(52) U.S. Cl.
USPC .......................................... 585/719; 585/709

(58) Field of Classification Search
None
See application file for complete search history.

(56) References Cited

U.S. PATENT DOCUMENTS 2,995,612 A * 8/1961 Hervert ......................... 585/899
7,285,698 B2 10/2007 Liu et al. ....................... 585/709
2004/0133056 A1 7/2004 Liu et al. ....................... 585/721
2005/0119423 A1 6/2005 Bergman et al. ................ 526/68
2006/0131209 A1* 6/2006 Timken et al. .................. 208/16
2011/0319693 A1* 12/2011 Hommeltoft et al. ......... 585/711
2013/0066133 A1* 3/2013 Cleverdon et al. ............ 585/721

FOREIGN PATENT DOCUMENTS

CN 101244972 8/2008 ................ C07C 2/58
WO WO9850153 11/1998 ............... B01J 31/02

* cited by examiner

*Primary Examiner* — Tam M Nguyen
(74) *Attorney, Agent, or Firm* — Charles W. Stewart

(57) ABSTRACT

The present invention provides process for preparing an alkylate comprising contacting in a reactor a hydrocarbon mixture comprising at least an isoparaffin and an olefin with an acidic ionic liquid catalyst under alkylation conditions to obtain an alkylate, which process further comprises: —withdrawing an alkylate-comprising reactor effluent from the reactor, wherein the reactor effluent comprises an ionic liquid phase and a hydrocarbon phase; —separating at least part the reactor effluent into a hydrocarbon phase effluent and a multiple-phase effluent in a centrifugal separation unit; —fractionating at least part of said hydrocarbon phase effluent into at least a stream comprising alkylate and a stream comprising isoparaffin.

18 Claims, 1 Drawing Sheet

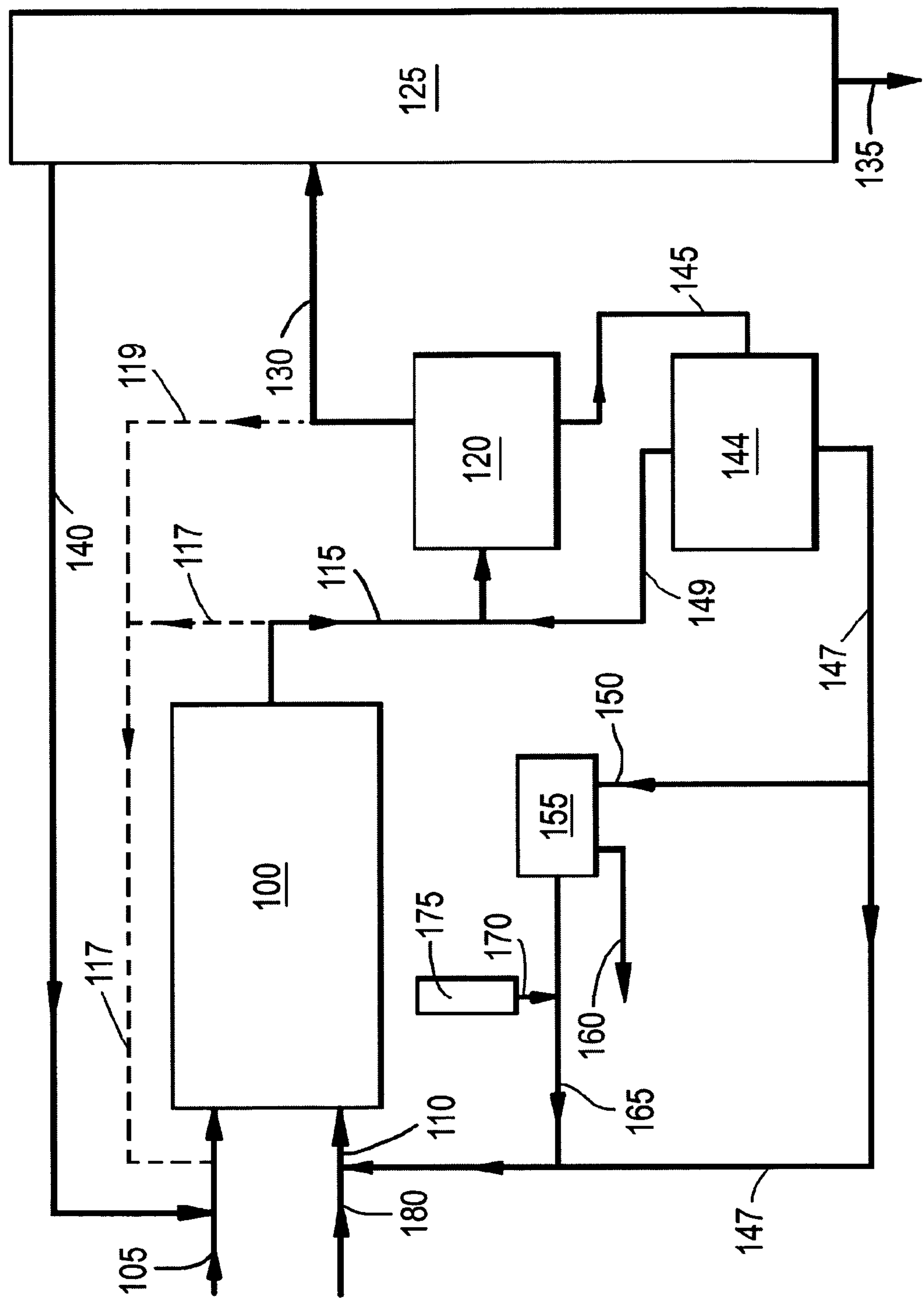
125
135
130
119
145
120
144
140
117
115
149
147
150
155
100
175
170
117
160
165
110
180
105
147

PROCESS FOR PREPARING AN ALKYLATE

PRIORITY CLAIM

The present application claims priority from PCT/EP2010/061488, filed 6 Aug. 2010, which claims priority from PCT/CN2009/000887, filed 6 Aug. 2009.

FIELD OF THE INVENTION

The present invention provides a process preparing an alkylate.

BACKGROUND OF THE INVENTION

There is an increasing demand for alkylate fuel blending feedstock. As a fuel-blending component alkylate combines a low vapour pressure with high octane properties.

Almost all alkylate is produced by reacting isobutane with butene in the presence of a suitable acidic catalyst. The most used catalysts are HF and sulphuric acid, although other catalysts such a solid acid catalyst have been reported. Recently, the alkylation of isoparaffins with olefins using an acidic ionic liquid catalyst has attracted attention as an alternative to HF and sulphuric acid catalysed alkylation processes.

In for instance U.S. Pat. No. 7,285,698 a process for manufacturing an alkylate oil is disclosed, which uses a composite ionic liquid catalyst to react isobutane with a butene. In the process of U.S. Pat. No. 7,285,698, isobutane and butene are supplied to a reactor and the alkylate is formed by contacting the reactants with a composite ionic liquid under alkylation conditions. The reactor effluent is separated and the ionic liquid phase is recycled to the reactor while the hydrocarbon phase is treated to retrieve the alkylate.

In for instance Liu et al. (Z. Liu, R. Zhang, C. Xu, R. Xia, Ionic liquid alkylation process produces high-quality gasoline, Oil and Gas Journal, vol 104, Issue 40, 2006) it is mentioned that it is possible to retrofit a sulphuric acid alkylation unit for use of an IL catalyst. However, it is mentioned that it is necessary to modify the settler unit to improve the separation of the reactor effluent, i.e. the ionic liquid catalyst and hydrocarbon phase.

In US2005/0119423, a process for preparing polyalphaolefins is disclosed using an ionic liquid catalyst. In the process of US2005/0119423, the reactor effluent is provided to a separator to obtain a polyalphaolefin-containing phase, which still comprises remaining ionic liquid catalyst. It is suggested in US2005/0119423, to mix the polyalphaolefin-containing phase with water to deactivate the catalyst and subsequently separate the polyalphaolefin-containing phase from the water in two additional sequential separation steps.

There is a need in the art for an ionic liquid alkylation process, which provides an improved separation of the reactor effluent.

SUMMARY OF THE INVENTION

It has now been found that the reactor effluent of an ionic liquid alkylation reactor can be efficiently separated in an acidic ionic liquid phase and a hydrocarbon phase using a centrifugal separation unit.

Accordingly, the present invention provides a process for preparing an alkylate comprising contacting in a reactor a hydrocarbon mixture comprising at least an isoparaffin and an olefin with an acidic ionic liquid catalyst under alkylation conditions to obtain an alkylate, which process further comprises:

- withdrawing an alkylate-comprising reactor effluent from the reactor, wherein the reactor effluent comprises an ionic liquid phase and a hydrocarbon phase;
- separating at least part the reactor effluent into a hydrocarbon phase effluent and a multiple-phase effluent in a centrifugal separation unit;
- fractionating at least part of said hydrocarbon phase effluent into at least a stream comprising alkylate and a stream comprising isoparaffin.

An advantage of the present invention is that there is no need to add water or additional compounds to the hydrocarbon phase comprising the alkylate. In addition, no catalyst is purposely deactivated or otherwise destroyed resulting in a lower catalyst consumption during the process.

BRIEF DESCRIPTION OF THE DRAWINGS

In FIG. 1 a schematic representation is given of a process according to the invention.

DETAILED DESCRIPTION OF THE INVENTION

In the process according to the invention an alkylate is prepared by reacting an isoparaffin with an olefin. The obtained alkylate is particularly suitable for gasoline blending purposes. In the process according to the invention the isoparaffin and the olefin are provided to a reactor. In the reactor a hydrocarbon mixture comprising isoparaffin and olefin is contacted with a catalyst suitable for alkylation. The hydrocarbon mixture comprises olefin, typically supplied externally, i.e. fresh olefin, and comprises isoparaffin. The isoparaffin may be externally supplied isoparaffin, i.e. fresh isoparaffin, and/or isoparaffin, which is recycled from any other part of the process. The fresh isoparaffin and olefin may be supplied to the process separately, however typically the fresh isoparaffin and the fresh olefin are provided to the reactor as a mixture comprising isoparaffin and olefin. In the present invention the catalyst is an acidic ionic liquid catalyst (herein below also referred to as catalyst).

Ionic liquids are known in the art for their ability to catalyse alkylation reactions. The catalyst used in the present invention is a composite ionic liquid comprising cations derived from a hydrohalide of an alkyl-containing amine or pyridine. Preferably, the cations comprise nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of suitable cations include triethyl-ammonium ($NEt_3H^+$) and methyl-diethyl-ammonium cations ($MeNEt_2H^+$) or

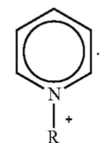

The anions of the composite ionic liquid are preferably aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulphate or nitrate to form a coordinate anion, in particular a coordinate anion derived from two or more metal halides, wherein at least one metal halide is an aluminium halide. Suitable further metal halides, sulphates or nitrates, may be selected from halides, sulphates or nitrates of metals selected from the group consisting of Group IB elements of the Periodic Table, Group IIB elements of the Periodic Table and transition elements of the Periodic Table. Examples or suitable metals include copper, iron, zinc, nickel, cobalt, molybdenum, or platinum. Preferably, the metal halides, sulphates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal improved alkylate product may be obtained. A method for preparing such catalyst is for instance described in U.S. Pat. No. 7,285,698. A particularly preferred catalyst is an acidic ionic liquid catalyst comprising a cation derived from triethyl-ammonium chloride and a coordinate anion derived from aluminium(III) chloride and copper(I) chloride.

As mentioned hereinabove, the hydrocarbon mixture comprising isoparaffin and olefin is contacted with the catalyst. The hydrocarbon mixture is mixed in the reactor with the catalyst to form a reaction mixture. As the reaction progresses the reaction mixture will, besides hydrocarbon reactants and acidic ionic liquid, additionally comprise products. Mixing of the hydrocarbon mixture and the catalyst may be done by any suitable means for mixing two or more liquids, including dynamic and static mixers. In contact with the catalyst, the isoparaffins and olefins react under alkylation conditions to form an alkylate. An alkylate-comprising reactor effluent (further also referred to a reactor effluent) is withdrawn from the reactor. The reactor effluent comprises a hydrocarbon phase and an ionic liquid phase. Reference herein to a hydrocarbon phase is to a phase comprising hydrocarbons and in the range of from 0 to 5 vol %, preferably 0 to 3 vol % of dissolved acidic ionic liquid, more preferably of from 0 to 0.5 vol % of dissolved acidic ionic liquid based on the total liquid weight of the hydrocarbon phase. Preferably, the hydrocarbon phase comprises in the range of from 95 to 100 vol % of hydrocarbons, preferably of from 97 to 100 vol % of hydrocarbon, based on the total liquid weight of the hydrocarbon phase. Reference herein to an ionic liquid phase is to an ionic liquid phase comprising acidic ionic liquid and in the range of from 0 to 20 vol %, preferably 0 to 10 vol % of dissolved hydrocarbons based on the total liquid weight to the ionic liquid phase. Preferably, the ionic liquid phase comprises in the range of from 80 to 100 vol %, preferably 90 to 100 vol % of acidic ionic liquid based on the total liquid weight to the ionic liquid phase. It will be appreciated that, although the hydrocarbon phase and the ionic liquid phase are immiscible, it is however possible that small amounts of hydrocarbons dissolve in the ionic liquid phase and vice versa that small amounts of acidic ionic liquid catalyst dissolve in the hydrocarbon phase.

The reactor effluent still comprises a substantial amount of unreacted isoparaffin. Therefore, part of the reactor effluent may be recycled to the reactor to maintain a high molar ratio of isoparaffin to olefin. In the process according to the present invention, at least part of the reactor effluent is provided to a centrifugal separation unit to separate the reactor effluent. The centrifugal separation unit may by any centrifugal separation unit suitable to separate at least two immiscible liquid phases. Preferably, the centrifugal separation unit is a cyclone type separation unit as such cyclone type separation units allow for a fast and continues separation of two immiscible liquid phases. In addition, due to the ability to reduce the time required for the separation compared to conventional settler units, centrifugal separation units can typically be less voluminous, requiring a smaller footprint and, more importantly, a much smaller inventories of liquefied light hydrocarbons, in particular isobutane. Preferably, the cyclone is a hydro-cyclone. Reference herein to a hydro-cyclone is to a cyclone designed for the separation of water-hydrocarbon mixtures. Reference herein to a centrifugal separation unit is to a separation unit that can separate two liquid phases on the basis of centrifugal forces. Reference herein to a separation unit is a separation unit comprising one separator, e.g. a cyclone, or two or more separators, e.g. two cyclones, aligned in parallel.

It will be appreciated that typical industrial scale centrifugal separation units cannot separate the reactor effluent into two or more effluents comprising only one phase, e.g. a hydrocarbon phase or an ionic liquid phase.

However, it has now been found that it is possible to separate the reactor effluent into a hydrocarbon phase effluent and a multiple-phase effluent comprising acid ionic liquid and hydrocarbon. Reference herein to a hydrocarbon phase effluent is to an effluent comprising a hydrocarbon phase and in the range of from 0 to 5 vol %, preferably of from 0 to 3 vol % of an ionic liquid phase, more preferably of from 0 to 0.5 vol % of an ionic liquid phase based on the total weight of the hydrocarbon phase effluent. Preferably, the hydrocarbon phase effluent comprises in the range of from 95 to 100 vol % of hydrocarbon phase, preferably of from 97 to 100 vol % of hydrocarbon phase, based on the total weight of the hydrocarbon phase effluent.

In the above-described separation of two immiscible phases, an essentially pure effluent is withdrawn from the separator comprising predominantly one phase, while it is accepted that the multiple-phase effluent contains significant amounts of both phases. Such a separation is within the normal skills of the skilled person in the art of centrifugal separations.

The hydrocarbon phase effluent still comprises a substantial amount of unreacted isoparaffin. Therefore, part of the hydrocarbon phase effluent may be recycled to the reactor to maintain a high ratio of isoparaffin or olefin. At least part of the hydrocarbon phase effluent from the separator is, without any intermediate chemical treatment, fractionated into at least a hydrocarbon stream comprising alkylate and a stream comprising isoparaffin. If desired the ionic liquid fraction in the hydrocarbon effluent may be lowered even further by subjecting the hydrocarbon phase effluent to a further physical separation treatment in a further centrifugal separation unit, such as a cyclone, or in a settler unit. Although, a settler unit may be relatively large in volume compared to e.g. a cyclone, if a settler unit is used as a second separator unit, the invention still provides an advantage as the second settler unit will be much smaller than a settler unit in a conventional process, which is used to separate the reactor effluent. Preferably, the process further comprises providing, prior to fractionating the hydrocarbon phase effluent, the hydrocarbon phase effluent to a further settler unit to remove additional ionic liquid.

The stream comprising isoparaffin is generally reused to form part of the isoparaffin feed provided to the process. This may be done by recycling at least part of the stream comprising isoparaffin and combining it with the isoparaffin feed to the process.

Reference herein to a chemical treatment is to a treatment resulting in the decomposition of one or more of the compounds in the essentially pure hydrocarbon effluent. The obtained hydrocarbon stream comprising alkylate may be used to prepare avgas or as a blending component for gasoline. Other hydrocarbon streams may also be obtained by fractionation of the essentially pure hydrocarbon effluent, such a n-paraffin-comprising stream.

The hydrocarbon phase effluent may be fractionated using any suitable method to fractionate a hydrocarbon stream. Preferably, the hydrocarbon phase effluent is fractionated using one or more distillation units.

In the process according to the invention it is preferred that at least part of the multiple-phase effluent obtained from the centrifugal separation unit is recycled back to the reactor. The multiple-phase effluent comprises most if not essentially all of the acidic ionic liquid catalyst, which was part of the reactor effluent. However, as describe hereinabove, the multiple-phase effluent also comprises significant amounts of hydrocarbons. Although, it is possible to recycle these hydrocarbons back to the reactor together with the acidic ionic liquid it is preferred to further separate the multiple-phase effluent in order to reduce the volume of the recycle.

Preferably, the process according to the invention further comprises providing the multiple-phase effluent to a second separation unit. The separation unit may by any separation unit suitable to separate two immiscible liquid phases. Examples of suitable separation units include settler separation units and centrifugal separation units. Preferably, the separator is a centrifugal separation units, more preferably a cyclone type separation units, as such separation units allow for a fast and continues separation of two immiscible liquid phases. Preferably, the cyclone is a hydro-cyclone. In the second separation unit, the multiple-phase effluent is separated into an ionic liquid phase effluent and another effluent, comprising hydrocarbons and acidic ionic liquid.

Reference herein to an ionic liquid phase effluent is to an effluent comprising ionic liquid phase and in the range of from 0 to 20 vol %, preferably 0 to 10 vol % of a hydrocarbon phase based on the total liquid weight to the ionic liquid phase effluent. Preferably, the ionic liquid phase effluent comprises in the range of from 80 to 100 vol %, preferably 90 to 100 vol % of ionic liquid phase based on the total liquid weight to the ionic liquid phase effluent.

At least part of the ionic liquid phase effluent is preferably recycled to the reactor.

The another effluent obtained from the second separation unit may be recycled to the first separation unit or be combined with the reactor effluent, which is provided to the first separation unit. By recycling the another effluent no catalyst or hydrocarbons are lost.

It has been observed that during the alkylation reaction solids are formed. Reference, herein to solids is to non-dissolved solid particles. The solids predominantly consist out of metals, metal compounds and/or metal salts which were originally comprised in the acidic liquid catalyst. Preferably, the solids comprise at least 10 wt % metal, i.e. either in metallic, covalently bound or ionic form, based the total weight of the solids, wherein the metal is a metal that was introduced to the process as part of the acidic ionic liquid catalyst. The solids may also comprise components, which were introduced into the reaction mixture as contaminants in the hydrocarbon mixture or the acidic ionic liquid. Alternatively, the solids may be the product of a chemical reaction involving any of the above-mentioned compounds.

The solids may have any size, however it was found that the solids typically have an average size of in the range of from 0.1 to 10 μm. In particular, at least 50% of the solids have a particle size below 5 μm, more particular 80% of the solids have a particle size below 5 μm based on the total number of solid particles.

Although, during mixing these solids are dispersed throughout the reaction mixture, upon separation of the reactor effluent it has been found that the solids, i.e. to a large extent, accumulate in the acidic ionic liquid catalyst-rich effluents, i.e. the multiple-phase effluent and/or ionic liquid phase effluent. This is due to the high density of the solids. When the multiple-phase effluent and/or ionic liquid phase effluent are, at least in part, recycled to the reactor, the solids accumulate in the reaction mixture, resulting in undesirably high solids content in the reaction mixture. A high solids content in the reaction mixture may for instance result in blockage of pathways or valves in the reactor and pipes to and from the separation unit, due to precipitation of solids. In addition, at high solids content the solids may agglomerate to from large aggregates, resulting in increased blockage risk.

Therefore, it is preferred that in the process according to the invention solids are removed from the multiple-phase effluent and/or ionic liquid phase effluent by providing the multiple-phase effluent and/or ionic liquid phase effluent to a third separation unit suitable for separation of solids and liquids and removing the solids from the multiple-phase effluent and/or ionic liquid phase effluent. In the present invention, at least part of the solids are removed from the multiple-phase effluent and/or ionic liquid phase effluent. Preferably, solids are removed from the multiple-phase effluent and/or ionic liquid phase effluent to an extent that the reaction mixture comprises at most 5 wt % of solids, preferably at most 2 wt % of solids, based on the total weight of the ionic liquid phase in the reactor. By removing the solids from the ionic liquid phase effluent rather than from the multiple-phase effluent, the liquid volume passing through the third separation unit is reduced, thus allowing for the use of a smaller separation unit.

The third separation unit may be any separation unit suitable for removing solids and liquids, including but not limited to filtration, precipitation and centrifugation processes. Such processes are well known in the art.

Due to the specific nature of ionic liquids it is preferred that the removal of the solids is performed at such a temperature that the acidic ionic liquid catalyst is liquid. In particular, it is preferred to remove the solids at a temperature in the range of from 5 to 80° C., more preferably of from 20 to 60° C. By removing the solids at elevated temperatures, the viscosity of the ionic liquid is low, which may be beneficial in view of the decreased time and power input required to obtained separation of the solids from the liquid.

The solids may be removed from the process in any form, typically the solids will be removed in the form of a slurry of solids. Such a slurry may comprise next to the solids for instance some residual acidic ionic liquid.

Although, it is believed that part of the catalyst is lost when forming the solids, the catalyst alkylation performance is not significantly affected. Loss of catalyst due to solids formation merely means that a small fraction of the total catalyst inventory is inactivated or lost, while the remainder of the catalyst remains unaffected.

Optionally, the catalyst in the multiple-phase effluent and/or ionic liquid phase effluent can be contacted with an acid, preferably a hydrogen halide, more preferably hydrogen chloride, to rejuvenate the catalyst. Preferably, the acidic ionic liquid catalyst is rejuvenated by recycling at least part of the multiple-phase effluent and/or ionic liquid phase effluent to the reactor and the at least part of the acid ionic liquid catalyst in the recycled effluent is rejuvenated by addition of hydrogen chloride to at least part of the recycled effluent.

More preferably, the hydrogen chloride is added to at least part of the ionic liquid phase effluent. By contacting the catalyst with hydrogen chloride after removal of most of the hydrocarbons, undesired chlorination of hydrocarbons is reduced. The hydrogen chloride reacts with the acidic ionic liquid catalyst. Hydrogen chloride is added until no hydrogen chloride is consumed any longer, i.e. until saturation. Hydrogen chloride consumption can be followed by monitoring the pressure. Preferably, the addition of hydrogen chloride is done in regular steps, optionally to batches of the ionic liquid to be rejuvenated, while measuring the pressure in between each addition step. By adding the hydrogen chloride in small steps the creation of an undesired hydrogen chloride gas cap upon saturation is reduced.

Preferably, the added gaseous hydrogen chloride is mixed with the recycled effluent to ensure a good contact between the gas and liquid phases.

The addition of hydrogen chloride may be done by injecting the hydrogen chloride into one or more units or into one or more streams passing from one unit to the next. Hydrogen chloride addition may for instance be done using a venturi absorber, preferably a venturi absorber located downstream from the means for removing solids.

As mentioned herein above, although some gaseous hydrogen chloride in the reactor may be tolerated, it is undesired to accumulate unreacted gaseous hydrogen chloride in the reaction system as a result of over-saturation of the acidic ionic liquid with hydrogen chloride. Residual gaseous hydrogen chloride may be purged from the reaction system by for instance flushing with an inert gas such as nitrogen. However, such process would require additional means for providing nitrogen gas and subsequent storage and treatment of hydrogen chloride-contaminated nitrogen gas. In addition, part of the hydrogen chloride is provided for rejuvenation is lost. Preferably, such hydrogen chloride accumulation is reduced by mixing additional spent acidic ionic liquid catalyst, e.g. in the form of a spent catalyst-comprising stream, into the rejuvenated acidic ionic liquid catalyst comprising recycled effluent, i.e. the recycled effluent comprising added hydrogen chloride. Reference, herein to spent acidic ionic liquid catalyst is to an acidic ionic liquid catalyst, which has been used as a catalyst in a chemical reaction and has not yet been rejuvenated with hydrogen chloride. By allowing the spent acidic ionic liquid to react with the gaseous hydrogen chloride present due to initial over-saturation, the remaining hydrogen chloride may be consumed. The spent ionic liquid catalyst may be introduced from an external source, however it is also possible to allow part of the ionic liquid phase effluent, multiple-phase effluent or other catalyst-comprising recycled effluent to bypass the rejuvenation and subsequently mix the rejuvenated and bypassed streams. For instance it is possible to rejuvenate the ionic liquid catalyst in the ionic liquid phase effluent and subsequently mix the effluent with the another effluent obtained from the second separator, as the another effluent still comprises spent, i.e. non-rejuvenated, ionic liquid catalyst.

The solids, which are removed from the process may be discarded, however it is preferred to reuse the components in the solids, for example in the preparation of fresh acidic ionic liquid catalyst.

In the process according to the invention, an isoparaffin and an olefin are reacted to form an alkylate by contacting the hydrocarbon mixture comprising isoparaffin and olefin with the catalyst under alkylation conditions.

Preferably, the hydrocarbon mixture comprises at least isobutane, isopentane or a mixture thereof as an isoparaffin. The hydrocarbon mixture preferably comprises at least an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

Isoparaffins and olefins are supplied to the process in a molar ratio, which is preferably 1 or higher, and typically in the range of from 1:1 to 40:1, more preferably 1:1 to 20:1. In the case of continuous reaction, excess isoparaffin can be recycled for reuse in the hydrocarbon mixture.

The alkylation conditions (or process conditions) are those known in the art for HF and sulphuric acid alkylation. Actual operational process conditions are among others dependent of the exact composition of the hydrocarbon mixture and catalyst.

The temperature in the reactor is preferably in the range of from −20 to 100° C., more preferably in the range of from 0 to 50° C. The temperature must in any case be above the melting temperature of the ionic liquid.

To suppress vapour formation in the reactor, the process is performed under pressure, preferably the pressure in the reactor is in the range of from 0.1 to 1.6 MPa.

The hydrocarbon mixture may be contacted with the catalyst in any suitable alkylation reactor. The hydrocarbon mixture may be contacted with the catalyst in a semi-continues or continuous process.

DETAILED DESCRIPTION OF THE DRAWINGS

In FIG. 1 a schematic representation is given of a process according to the invention.

In FIG. 1, a hydrocarbon mixture, comprising olefin and isoparaffin, e.g. butene and isobutane, is provided to reactor 100 through line 105. Acidic ionic liquid catalyst is also provided to reactor 100 through line 110. In reactor 100, the hydrocarbon mixture and catalyst are mixed under alkylation conditions. Through line 115, an alkylate-comprising reactor effluent comprising solids is withdrawn from the reactor. Part of this effluent may be directly recycled to the reactor or combined with line 105 via recycle line 117. At least part of the effluent is supplied to first centrifugal separation unit 120, e.g. a cyclone. In first centrifugal separation unit 120, the reactor effluent is separated in a hydrocarbon phase effluent and multiple-phase effluent under influence of the centrifugal forces. Part of the hydrocarbon phase effluent may be directly recycled to the reactor or combined with line 105 via recycle lines 117 and 119. At least part of the hydrocarbon phase effluent is provided to fractionator 125 through line 130. From the bottom of fractionator 125, an alkylate-comprising product is retrieved through line 135. The alkylate product can be used for instance for fuel blending purposes. Additionally, a stream comprising isoparaffin is retrieved from fractionator 125, which is recycled via line 140 to become part of the isobutane feed in line 105. Other hydrocarbon-comprising streams (not shown) may also be retrieved from fractionator 125.

The multiple-phase effluent is provided to second separation unit 144, e.g. a cyclone, via line 145. In second separation unit 144, the multiple-phase effluent is separated in to an ionic liquid phase effluent and another effluent. The another effluent may withdrawn from second separation unit 140 via line 149, be combined with line 115 and recycled to the first separation unit. The ionic liquid phase effluent can be recycled to the reactor via line 147. Part or all of the ionic liquid phase effluent can be diverted from line 147 by line 150 to third separation unit 155, e.g. a centrifuge. In centrifuge 155, solids are removed from the ionic liquid phase effluent under influence of the centrifugal forces, and are retrieved via line 160. The remaining ionic liquid phase effluent exits centrifuge 155 via line 165. Optionally, hydrochloride gas is provided to the ionic liquid phase effluent via line 170 from gas container 175. Optionally, a mixing device (not shown), e.g. a venturi absorber, is used to mix the hydrogen chloride gas into line 165. By allowing part of the catalyst to bypass the hydrogen chloride rejuvenation via line 147, any remaining gaseous hydrogen chloride may react with the ionic liquid catalyst in line 147 when lines 165 and 147 come together. It is also possible to provide a bypass (not shown) around the intersection of lines 165 and 170. In this way solids may be removed also from the ionic liquid catalyst, which is not rejuvenated.

The ionic liquid phase effluent is subsequently directed back to reaction zone 100. If necessary additional fresh acidic ionic liquid catalyst or externally supplied spent acidic ionic liquid catalyst can be provided to reaction zone 100 via line 180.

EXAMPLES

The invention is illustrated by the following non-limiting examples.

Example 1

In order to show the effectiveness of using a cyclone to separate the reactor effluent rather than a conventional settler, a sample reactor effluent, comprising a mixture of hydrocarbon reactants and products and ionic liquid catalyst was separated using a cyclone.

The sample reactor effluent comprises hydrocarbons and ionic liquid catalyst in a volume ratio of 1:1.05. The operating temperature was maintained between 30 and 50° C. and the operating pressure was maintained between 0.1 to 0.5 MPa. The maximum feed rate of sample reactor effluent to the cyclone was 2 $m^3$/hr.

40 vol % of the sample reactor effluent was retrieved as hydrocarbon phase effluent. The remaining 60 vol % of the sample reactor effluent was retrieved as ionic liquid phase effluent.

The hydrocarbon phase effluent comprised:

95.5 vol % of hydrocarbons; and 4.5 vol % of ionic liquid, based on the volume of the hydrocarbon phase effluent.

The ionic liquid phase effluent comprised:

17.7 vol % of hydrocarbons; and 82.3 vol % of ionic liquid, based on the volume of the ionic liquid phase effluent.

Using one separator approximately 79 vol % of the hydrocarbons originally provided in the sample reactor effluent were recovered in the hydrocarbon effluent.

In case the hydrocarbon phase effluent is further treated in a further settler unit, the size of volume of the settler unit is only 40% of a settler unit used to separate the whole reactor effluent.

What is claimed is:

1. A process for preparing an alkylate comprising contacting in a reactor a hydrocarbon mixture comprising at least an isoparaffin and an olefin with an acidic ionic liquid catalyst under alkylation conditions to obtain an alkylate, which process further comprises:

withdrawing an alkylate-comprising reactor effluent from the reactor, wherein the reactor effluent comprises an ionic liquid phase and a hydrocarbon phase;

separating at least part the reactor effluent into a hydrocarbon phase effluent and a multiple-phase effluent in a centrifugal separation unit;

fractionating at least part of said hydrocarbon phase effluent into at least a stream comprising alkylate and a stream comprising isoparaffin;

providing the multiple-phase effluent to a second separation unit;

separating the multiple-phase effluent into an ionic liquid phase effluent and another effluent, wherein at least part of the ionic liquid phase effluent is recycled to the reactor.

2. A process according to claim 1, wherein the second separation unit is a centrifugal separation unit.

3. A process according to claim 1, wherein the second separation unit is a settler separation unit.

4. A process according to claim 2, wherein the second centrifugal separation unit is a cyclone separation unit.

5. A process according to claim 4, wherein the hydrocarbon phase effluent comprises a hydrocarbon phase and in the range of from 0 to 3 vol % of ionic liquid phase, based on the total liquid weight of the hydrocarbon phase effluent.

6. A process according to claim 5, wherein the ionic liquid phase effluent comprises ionic liquid phase and in the range of from 0 to 20 vol % of hydrocarbon phase, based on the total liquid weight of the ionic liquid phase effluent.

7. A process according to claim 6, wherein the ionic liquid phase effluent comprises solids, which process further comprises:

providing the ionic liquid phase effluent to a third separation unit suitable for separating solids and liquids; and removing at least part of the solids from the ionic liquid phase effluent.

8. A process according to claim 7, wherein the process further comprises:

providing, prior to fractionating the hydrocarbon phase effluent, the hydrocarbon phase effluent to a further settler unit to remove additional ionic liquid.

9. A process according to claim 8, wherein the isoparaffin is isobutane and/or isopentane.

10. A process according to claim 9, wherein the hydrocarbon mixture comprises an olefin comprising in the range of from 3 to 6 carbon atoms.

11. A process according to claim 10, wherein the acidic ionic liquid catalyst is a composite ionic liquid comprising of cations derived from a hydrohalide of an alkyl-containing amine or pyridine, anions being multiple-phase coordinate anions derived from two or more metal halides, wherein at least one metal halide is an aluminium halide and any further metal halide is a halide of a metal selected from the group consisting of Group IB elements of the Periodic Table, Group IIB elements of the Periodic Table and transition elements of the Periodic Table.

12. A process according to claim 10, wherein to the catalyst comprises aluminium chloride and copper (I) chloride or copper (II) chloride.

13. A process according to claim 4, wherein the hydrocarbon phase effluent comprises a hydrocarbon phase and in the range of from 0 to 0.5 vol % of ionic liquid phase, based on the total liquid weight of the hydrocarbon phase effluent.

14. A process according to claim 3, wherein the ionic liquid phase effluent comprises ionic liquid phase and in the range of from 0 to 10 vol % of hydrocarbon phase, based on the total liquid weight of the ionic liquid phase effluent.

15. A process according to claim 6, wherein the multiple-phase effluent comprises solids, which process further comprises:

providing the multiple-phase effluent to a third separation unit suitable for separating solids and liquids; and removing at least part of the solids from the multiple-phase effluent.

16. A process according to claim 3, wherein the hydrocarbon mixture comprises an olefin comprising in the range of from 4 to 5 carbon atoms.

17. A process according to claim 1 wherein the first centrifugal separation unit and the second centrifugal separation unit are both cyclone separation units.

18. A process according to claim 17, wherein the cyclone separation units are hydro-cyclones.

* * * * *